US00PP32003P2

(12) United States Plant Patent
LaBonte

(10) Patent No.: US PP32,003 P2
(45) Date of Patent: Jul. 21, 2020

(54) SWEETPOTATO PLANT NAMED 'LA17-54'

(50) Latin Name: ***Ipomoea batatas* (L.) Lam.**
Varietal Denomination: LA17-54

(71) Applicant: The Board of Supervisors of Louisiana State University and Agricultural and Mechanical College, Baton Rouge, LA (US)

(72) Inventor: Don R. LaBonte, Baton Rouge, LA (US)

(73) Assignee: THE BOARD OF SUPERVISORS OF LOUISIANA STATE UNIVERSITY AND AGRICULTURAL AND MECHANICAL COLLEGE, Baton Rouge, LA (US)

( * ) Notice: Subject to any disclaimer, the term of this patent is extended or adjusted under 35 U.S.C. 154(b) by 0 days.

(21) Appl. No.: 16/350,990

(22) Filed: Feb. 8, 2019

(51) Int. Cl.
*A01H 5/12* (2018.01)
*A01H 6/00* (2018.01)

(52) U.S. Cl.
USPC ..... Plt./258

(58) Field of Classification Search
USPC ..... Plt./258, 263.1, 226, 256
CPC ... A01H 5/06; A01H 5/02; A01H 5/12; A01H 5/00; A01H 5/04; A01H 6/00
See application file for complete search history.

*Primary Examiner* — June Hwu
(74) *Attorney, Agent, or Firm* — Baker Donelson

(57) ABSTRACT

A new variety of sweetpotato, identified as 'LA17-54', is disclosed having disease resistance to *Fusarium* wilt; an orange flesh, red-copper skin storage root and attractive purple, red-hued and green leaves with purple venation and purple vines.

3 Drawing Sheets

Genus and species name: *Ipomoea batatas* (L.) Lam.
Variety denomination: 'LA17-54'.

BACKGROUND OF THE INVENTION

Sweetpotatoes, unlike Irish potatoes (*Solanum tuberosum*), are not tuber propagated plants. A "tuber" is a short, thickened portion of an underground branch. Along a tuber "eyes" are found, each of which comprises a ridge bearing a scale-like leaf (analogous to a branch leaf) having minute meristematic buds in the axial of the leaf. By contrast, sweetpotato roots are developmentally and anatomically true roots, lacking meristematic buds, and are not derived from an underground branch. Sweetpotatoes do not form tubers.

SUMMARY OF THE INVENTION

This invention pertains to a new and distinct variety of sweetpotato. This new and distinct sweetpotato variety demonstrates superior disease resistance to *Fusarium* wilt and exhibits a storage root with orange flesh and has ornamental characteristics for foliage. It also demonstrates dark purple, red hued and green leaves in comparison to '05-111' with green leaves.

This new and distinct sweetpotato variety is characterized by a storage root with orange flesh, red-copper skin and purple, red-hued and green leaves.

DETAILED BOTANICAL DESCRIPTION

This new variety of sweetpotato, named 'LA17-54', resulted from an open pollinated cross performed in 2016 to the female parent 'LA16-82' (not patented). The female parent 'LA16-82' has dark green foliage but not purple. 'LA16-54' was developed to provide a variety with storage root characteristics similar to '05-111' (U.S. Plant Pat. No. 23,761 P3) and attractive foliage for ornamental use.

Plants of 'LA17-54' and variety '05-111' can be differentiated. Many leaves of 'LA17-54' are entire and purple [7.5 P (purple) (2/2)] and '05-111' has an entire green leaf. Roots of 'LA17-54' are red-copper skin [7.5 Y (yellow) R (red) (7/10)] and can be differentiated from the light to medium rose skin of '05-111'. Color terminology used herein is in accordance with the MUNSELL® Book of Color (2003 Edition, Munsell Color, GretagMacbeth LLC, 617 Little Britain Road, New Windsor, N.Y. 12553-6148). The color descriptions and color illustrations are as nearly true as is reasonably possible. However, it is understood that both color and other phenotypic expressions described herein may vary from plant to plant with differences in growth, environment and cultural conditions, without any change in the genotype of the variety 'LA17-54'.

'LA17-54' roots were stored during the winter in Chase, La. 'LA17-54' was planted the following spring, resulting in approximately 8-10 sprouts per root. Cuttings from the sprouts were transplanted successfully for asexual reproduction in Chase, La. Asexual propagation of the new cultivar by cuttings has shown that the unique features of this new sweetpotato were stable and that the plant reproduced true to type in successive generations of asexual propagation. Plants described herein were 90 days in age from planting in full sun field plantings.

Figure 1:
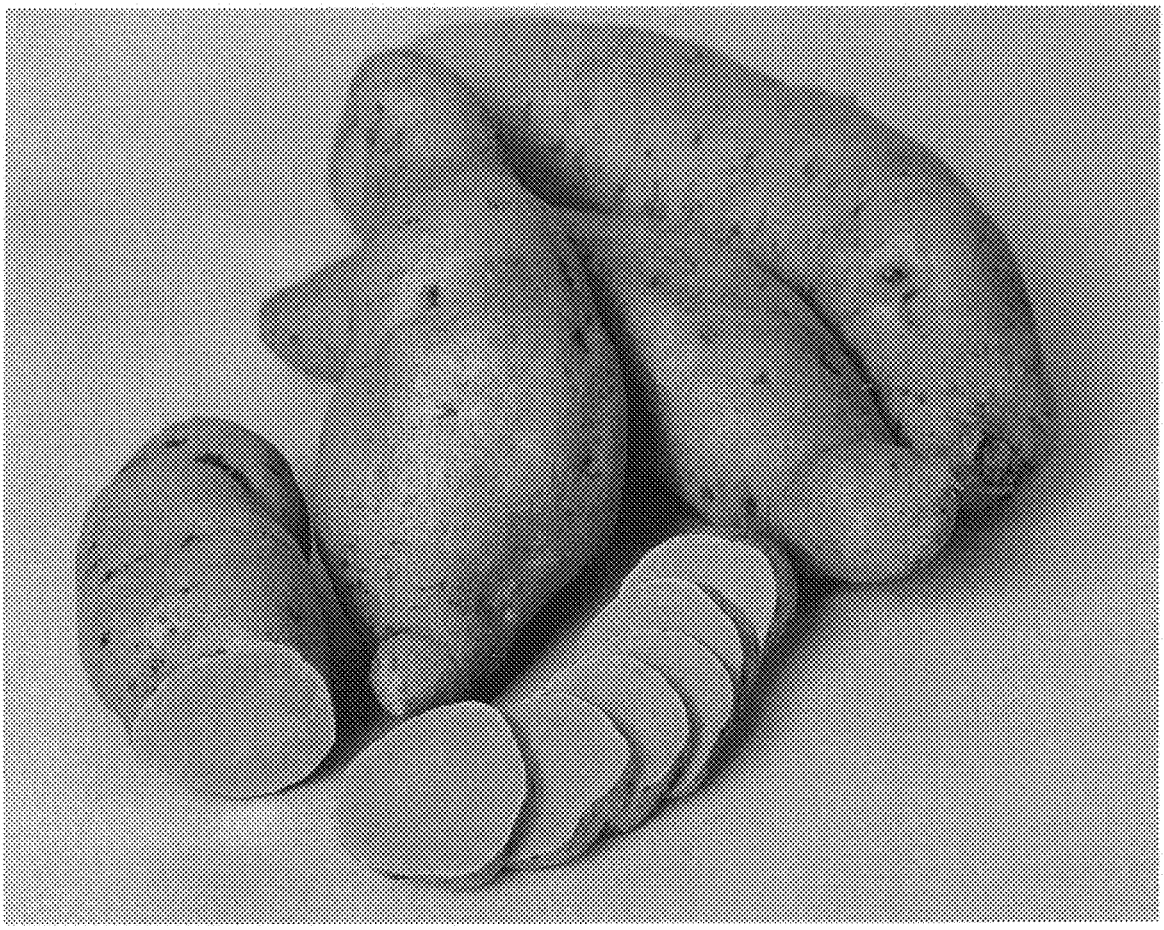
FIG. 1 is a color photograph of the fleshy root form of the novel variety of sweetpotato identified as 'LA17-54'.

FIG. 1 depicts the fleshy root form of the 'LA17-54' sweetpotato. The skin is a red-copper and differs from the light to medium rose '05-111', both at harvest and after several months of storage as shown in Table 1. No eyes or longitudinal grooving is present.

Figure 2:
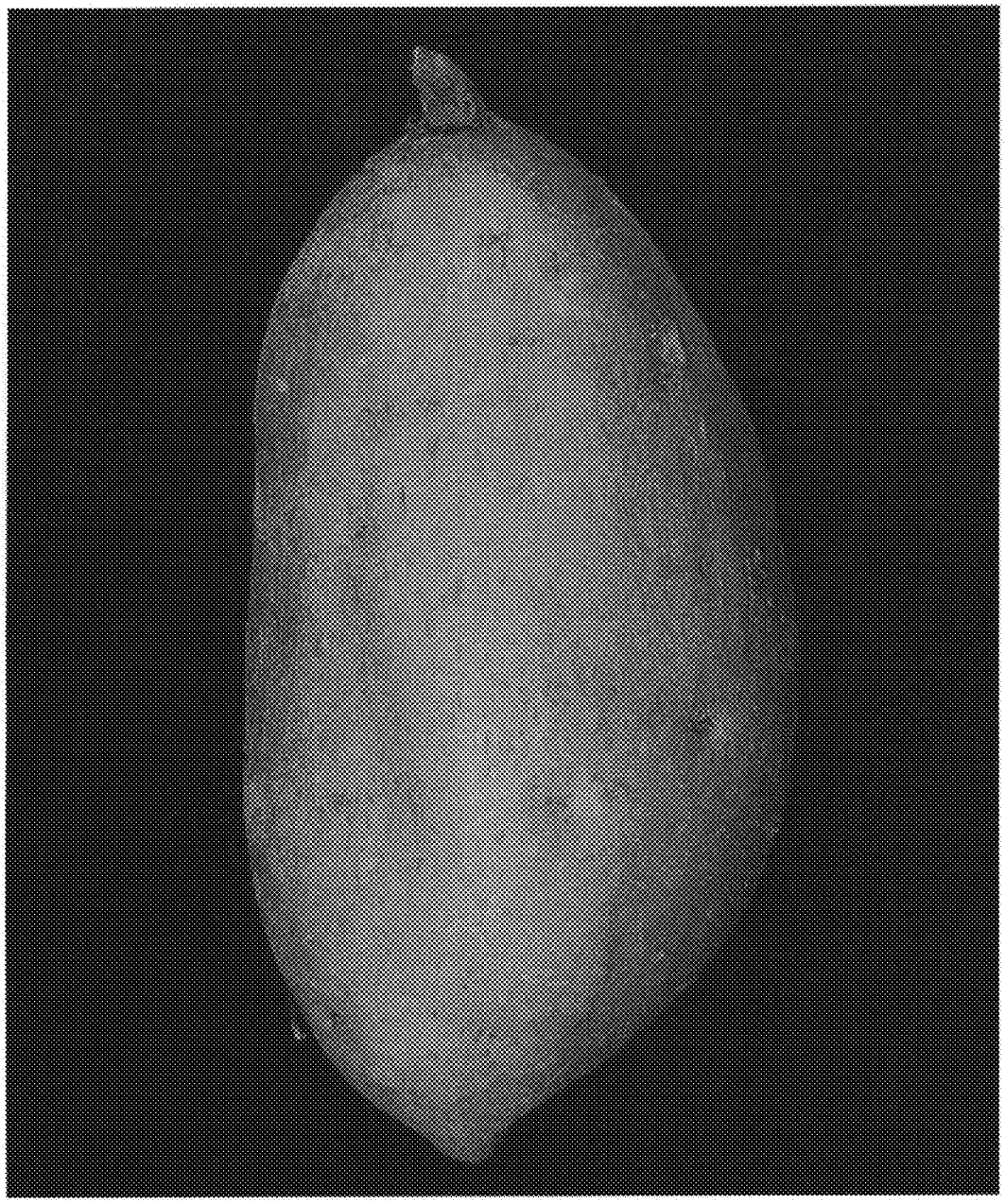
FIG. 2 is a color photograph of the fleshy root form of the sweetpotato variety identified as '05-111'.

MUNSELL® Book of Color values for skin and flesh for both 'LA17-54' and '05-111' storage roots are shown in Table 1. The '05-111' sweetpotato is depicted in FIG. 2. The skin for both 'LA17-54' and '05-111' was smooth. The 'LA17-54' cortex was 3 mm in depth and the color similar throughout. The flesh of 'LA17-54' is orange and comparable to orange flesh '05-111'.

TABLE 1

| Variable | Variety | Color |
|---|---|---|
| Skin | 'LA17-54' | 7.5 Y (yellow) R (red) 7/10 |
| | '05-111' | 2.5 Y (yellow) R (red) 6/6 |
| Flesh | 'LA17-54' | 5 Y (yellow) R (red) 7/10 |
| | '05-111' | 2.5 Y (yellow) R (red) 7/8 |

Figure 3:
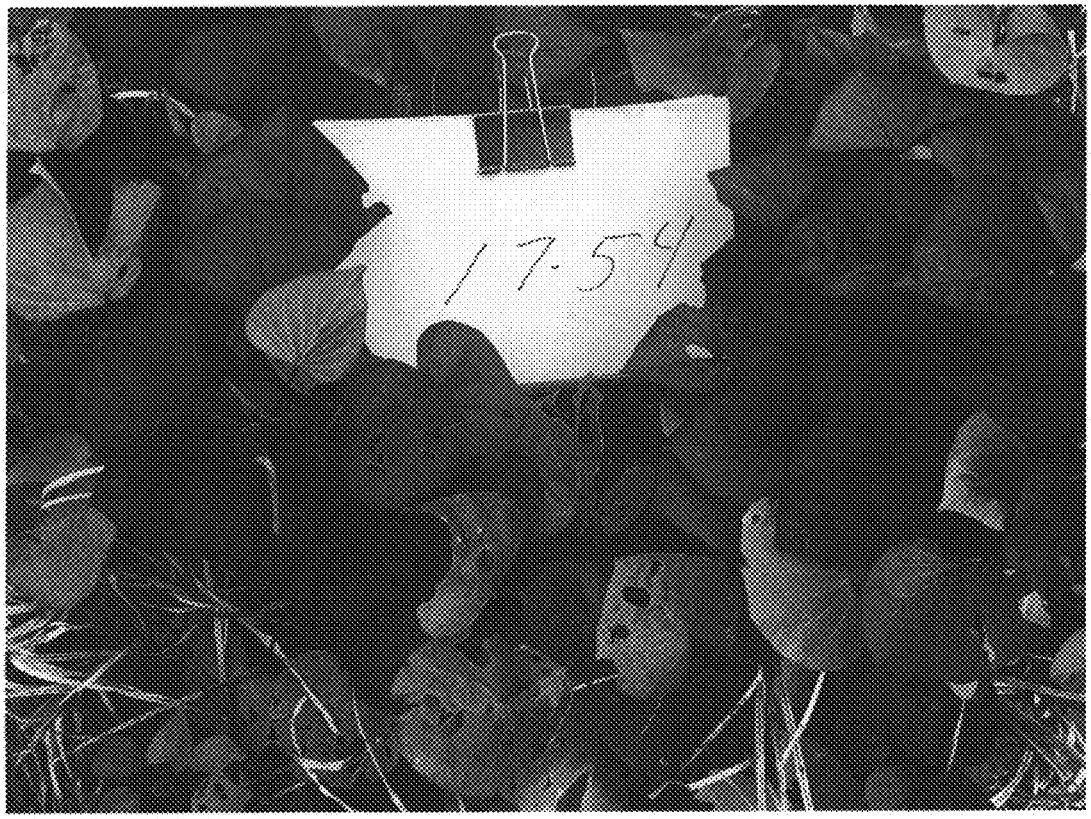
FIG. 3 is a color photograph of the canopy biomass of the novel variety of sweetpotato identified as 'LA17-54' with card stating '17-54'.

FIG. 3 depicts the canopy biomass of 'LA17-54' sweetpotato. 'LA17-54' has round, green-stemmed vines which change quickly from a green apex [2.5 G (green) Y (yellow) (4/6)] to purple vines [2.5 R (red) P (purple) (2/6)] 0.6 cm from the apex and extends to the crown of the roots. The apex has weak purple [10 P (purple) (3/6)] undertones. The first 4 cm from the apex is weakly pubescence before becoming glabrous. The 'LA17-54' canopy biomass appears to be reduced in comparison to '05-111'. The 'LA17-54' canopy architecture was 16 cm in height from the soil surface and semi-upright. For 'LA17-54', five main vines arose from the main stem near the soil surface. The stem giving rise to these vines was 0.12 cm in diameter; the 5 lateral vines were 76 cm in length with diameters of about 0.6 cm at 65 cm from the base and diameters of about 0.5 cm at the first internode of the first fully developed leaf from the apex. The spread is less than '05-111' and semi-compact. Four lateral branches arose from each of the main vines. At the first internode from the apex, the internode length was about 1.2 cm between the first and second fully developed leaves. Internode lengths for other sections of the vine averaged about 2.2 cm. Unfolded immature leaves and newly open leaves were light green [2.5 G (green) Y (yellow) (4/6)] for the adaxial and abaxial surface, which change over three nodes from the apex for the adaxial surface to a dark purple [2.5 R (red) P (purple) (2/2)] and a dark purple abaxial surface [2.5 P (purple) 2/2]. Mature older leaves are dark purple [7.5 P (purple) (2/2)] for the adaxial surface and purple for the abaxial surface [7.5 R (red) P (purple) (3/4)]. Older leaves have faded purple and take on a red hue [10 R (red) P (purple) (2/6)]. Other leaves become green [7.5 G (green) Y (yellow) (3/6)]. A mix of leaf colors add to ornamental characteristics of 'LA17-54'. Mature leaves five nodes from the apex had an acute apex and mostly a cordate base and entire leaf. Leaf margins are entire. Leaves are undulating, slightly wrinkled and have weak rugose texture on adaxial and abaxial surface. Mature leaves were about 6.0 cm long and 7.9 cm wide. Adaxial and abaxial veins were in a pinnate venation pattern and very large purple [7.5 P (purple) (2/2)] coloration. The petiole was purple [2.5 R (red) P (purple) (2/6)]. The coloration extended from the leaf veins to the petiole in a continuous fashion. The petiole was 7.5 cm long at five nodes from the apex, and 2 mm in diameter at 5 cm from the leaf junction. The dormant nodal meristem was purple [2.5 R (red) P (purple) (2/6)].

A typical inflorescence of 'LA17-54' displayed two clusters of six flowers per peduncle. Peduncles were purple [5 P (purple) (2/4)], about 15 cm long, and about 3.4 mm in diameter. Individual flowers were about 3.5 cm long from the base of the calyx, and the corolla was 4.2 cm wide at the opening. The fused flower petals formed a pentagonal pattern with smooth edges. The inner throat of the corolla is purple [5 P (purple) (3/6)]. The inner and outer limbs of the corolla (corollas outermost area, distal from the calyx) were light purple [10 P (purple) (6/4)]. The five sepals comprising the calyx were elliptic with a cordate apex and purple [10 P (purple) (6/4)]; three of these sepals were about 12.5 mm long and 6.0 mm wide. Two other sepals (interspersed) were about 9 mm long and 3.5 mm wide. Sepal margins were entire. Stigmata were about 1.7 cm long and light purple [10 P (purple) (8/4)] at the base before fading. Three stamens were inferior to the stigmata and 2 were superior to the stigmata. A slight fragrance was present. Mature seed capsules are round and 6.0-6.2 mm in length and width, and seeds are 3.5 mm round. One black [neutral 1.75] seed is produced on average per capsule.

EXAMPLE 1

Tests Conducted

To confirm that 'LA17-54' was a new ornamental variety with storage roots, controlled tests (e.g., pathogen responses and yield) were conducted in Baton Rouge, La. '05-111' was selected for comparison because of its importance in commercial United States orange flesh sweetpotato acreage. Diseases that commonly affect the growth of sweetpotatoes were selected to test for pathogen responses in both varieties. 'LA17-54' and '05-111' were resistant to *Fusarium* wilt or stem rot caused by *Fusarium oxysporum* Schlect. f. sp. *batatas* (Wollenw.) Snyd. & Hans.

Nematode reproduction was measured in greenhouse tests. 'LA17-54' and '05-111' were susceptible to race 3 of the southern root-knot nematode *Meloidogyne incognita* (Kofoid & White 1919) Chitwood 1949.

Storage roots have a storage life similar to '05-111'. There are no data on shipping or storage root market use.

'LA17-54' is drought and heat tolerant like '05-111' and succumbs to death at freezing like '05-111'.

'LA17-54' has not been tested for novel insect resistance.

To determine yield production, a complete-block trial using three replications of 'LA17-54' and '05-111' was conducted in 2018 in Louisiana. 'LA17-54' and '05-111' sweetpotato plants were transplanted in randomized complete-block trials at 31 cm spacings. Each block/plot was fertilized with approximately 250 pounds per acre of a mixed fertilizer comprising 13% N, 13% $P_2O_5$, and 13% $K_2O$. 'LA17-54' was compared to '05-111' at a transplanting date in June. Average yields were measured for the following grades of roots: U.S. #1 (51-89 mm in diameter, 76-229 mm long); Canner (25-51 mm in diameter, 51-178 mm long); and Jumbo (larger than U.S. #1 in diameter, length or both, and without objectionable defects). A typical marketable root of 'LA17-54' was 180-190 mm long, 60-70 mm in diameter; mostly irregular and slightly elongate in shape. The base or distal end tended to be more elongated in comparison to slightly rounder apex (proximal end). U.S. #1 roots typically weighed 150-190 g.

A mid-season transplanting date trial was conducted at Gilbert, La. in 2018. 'LA17-54' and '05-111' were transplanted on Jun. 19, 2018 and harvested on Oct. 19, 2018 (123 days after planting). Average yields, measured as Metric Tons per Hectare ($MT \cdot ha^{-1}$), are shown for 'LA17-54' and '05-111' in Table 2.

TABLE 2

Mid-season transplant date yield trial.

| Selection | US #1† | Canners† | Jumbos† | TMY‡† |
|---|---|---|---|---|
| 'LA17-54' | 6.35a | 11.23a | 0.00a | 17.57a |
| '05-111' | 10.98a | 11.23a | 0.00a | 22.21a |

†Average yields in $MT \cdot ha^{-1}$ of varieties followed by a common letter do not differ significantly ($P < 0.05$) according to Duncan's Multiple Range Test.
TMY‡ = total marketable yield As shown in Tables 2, 'LA17-54' was less competitive in yield in comparison to '05-111' for the U.S. #1 grade and comparable for the canner grade. 'LA17-54' had harvestable roots approximately 120-130 days after planting, which is typical development time for sweetpotatoes and comparable to '05-111'. 'LA17-54' is intended for the ornamental market. 'LA17-54' demonstrates fair yield in comparison to a commercial fresh-market variety.

'LA17-54' should be a valuable commercial ornamental sweetpotato variety. 'LA17-54' has fair yield in comparison to '05-111' and represents a unique canopy type which produces edible red-copper skin, orange flesh roots.

What is claimed is:

1. A new and distinct variety of *Ipomoea batatas* plant named 'LA17-54' as described and illustrated in the specification herein.

* * * * *